(12) United States Patent
Rust et al.

(10) Patent No.: US 9,678,702 B2
(45) Date of Patent: Jun. 13, 2017

(54) ULTRASOUND IMAGE DISPLAY SET-UP FOR REMOTE DISPLAY TERMINAL

(71) Applicant: KONINKLIJKE PHILIPS N.V., Eindhoven (NL)

(72) Inventors: David Rust, Seattle, WA (US); Karl Erhard Thiele, Andover, MA (US); Kevin Bradley, Bothell, WA (US); Earl M. Canfield, Snohomish, WA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 52 days.

(21) Appl. No.: 14/402,353

(22) PCT Filed: May 10, 2013

(86) PCT No.: PCT/IB2013/053788
§ 371 (c)(1),
(2) Date: Nov. 20, 2014

(87) PCT Pub. No.: WO2013/175337
PCT Pub. Date: Nov. 28, 2013

(65) Prior Publication Data
US 2015/0153990 A1   Jun. 4, 2015

Related U.S. Application Data

(60) Provisional application No. 61/650,241, filed on May 22, 2012.

(51) Int. Cl.
*G06F 19/00* (2011.01)
*G06F 3/14* (2006.01)
(Continued)

(52) U.S. Cl.
CPC ............ *G06F 3/1423* (2013.01); *A61B 8/463* (2013.01); *A61B 8/565* (2013.01); *G01S 7/003* (2013.01);
(Continued)

(58) Field of Classification Search
CPC ...................................................... G06F 19/34
See application file for complete search history.

(56) References Cited

U.S. PATENT DOCUMENTS 5,474,073 A   12/1995   Schwartz
5,485,842 A    1/1996   Quistgaard
(Continued)

FOREIGN PATENT DOCUMENTS

RU        2152173 C1    10/2000
WO     2006008664 A1     1/2006
(Continued)

*Primary Examiner* — Alexander Eisen
*Assistant Examiner* — Cory Almeida

(57) ABSTRACT

An ultrasound system enables simplified setup of a remote terminal for display of ultrasound images acquired by the ultrasound system. An image acquired by the ultrasound system is processed by or with display parameters for different viewing conditions or devices, such as display gamma correction, ambient lighting, or image quality. A plurality of versions of an image with slightly different display appearances are exported to the remote terminal, where a viewer can view all of the image versions simultaneously. The viewer selects the best image, and the display characteristics of the selected image are used for images subsequently exported from the ultrasound system to the remote terminal.

15 Claims, 5 Drawing Sheets

(51) Int. Cl.
  *G01S 7/00*   (2006.01)
  *G01S 7/52*   (2006.01)
  *A61B 8/00*   (2006.01)

(52) U.S. Cl.
  CPC ........ *G01S 7/52053* (2013.01); *G06F 19/321* (2013.01); *G06F 19/3412* (2013.01); *A61B 8/464* (2013.01); *F04C 2270/041* (2013.01); *G01S 7/52084* (2013.01)

(56) References Cited

U.S. PATENT DOCUMENTS

| | | | |
|---|---|---|---|
| 5,720,291 A | 2/1998 | Schwartz | |
| 5,833,613 A | 11/1998 | Averkiou | |
| 6,013,032 A | 1/2000 | Savord | |
| 6,186,950 B1 | 2/2001 | Averkiou | |
| 6,375,617 B1 | 4/2002 | Fraser | |
| 6,692,438 B2 | 2/2004 | Skyba | |
| 6,951,543 B2 | 10/2005 | Roundhill | |
| 2004/0061889 A1* | 4/2004 | Wood | G06F 19/321 358/1.15 |
| 2005/0275666 A1* | 12/2005 | Nagarajan | H04N 1/00209 345/660 |
| 2008/0097203 A1* | 4/2008 | Nereson | G01S 7/52053 600/437 |
| 2010/0189329 A1 | 7/2010 | Mo et al. | |
| 2011/0196237 A1 | 8/2011 | Pelissier et al. | |
| 2013/0012820 A1* | 1/2013 | Brown | A61B 8/465 600/443 |

FOREIGN PATENT DOCUMENTS

| | | |
|---|---|---|
| WO | 2008007301 A2 | 1/2008 |
| WO | WO-2011117788 * | 9/2011 |

* cited by examiner

ULTRASOUND IMAGE DISPLAY SET-UP FOR REMOTE DISPLAY TERMINAL

This application is the U.S. National Phase application under 35 U.S.C. §371 of International Application No. PCT/IB2013/053788, filed on May 10, 2013, which claims the benefit of U.S. Provisional Application No. 61/650,241 filed on May 22, 2012. These applications are hereby incorporated by reference herein.

This invention relates to medical diagnostic ultrasound systems and, in particular, to the export and display of images from an ultrasound system to a remote display terminal such as a review station on a PACS (picture archiving and communication) system.

A typical ultrasonic imaging system will have dozens of control setting which can be adjusted by a user to best display an image of anatomy of the body. For instance, when imaging tissue a sonographer will be able to set the line density, focal zones, dynamic range, transmit and receive frequencies, resolution penetration, transmit power, sector width, grayscale mapping, number of multilines, and numerous other imaging variables. When imaging blood flow in the colorflow mode some of the imaging variables which may be adjusted are wall filter settings, color map, frame rate, velocity range, frequency compounding, filter settings, and Doppler steering angle. With so many possible settings it is not surprising that ultrasound systems have control software that stores parameter presets for different types of imaging exams. A sonographer starting an obstetrical exam, for example, can select the presets for an OB exam and the ultrasound system will invoke a set of presets commonly used for most OB exams. The sonographer may be satisfied and use the system-selected presets, or can adjust the preset values and save the new set of presets as his or her preferred presets for a particular patient or type of exam.

Unless a sonographer is always satisfied by the system presets for an exam type, even customizing and saving sets of preset parameters for different exams can be a time consuming task. Moreover even custom presets can become unsatisfactory or obsolete as equipment is upgraded and new probes become available for standard exams. However, U.S. Pat. No. 6,951,543 (Roundhill) has provided a solution to this problem. That is to process an ultrasound image with a variety of different parameter values, such as the standard system preset values and common variations thereof. The sonographer does not have adjust numerous parameters and controls and see what difference each incremental or new parameter variation produces. Instead, the sonographer views a gallery of images, each of which has been processed by at least a slightly different set of acquisition or image processing parameters. The sonographer then simply picks the image that looks the best, and the parameters of that image are then applied for a particular exam. The selection process is far simpler than painstakingly adjusting numerous ultrasound system parameters.

The reading of ultrasound images in order to arrive at a diagnosis of a disease condition often does not occur on the ultrasound system which acquired the images. In many hospitals and clinics a sonographer may acquire the ultrasound images by scanning a patient, and the images of the patient are then transmitted to a diagnostic workstation or terminal where a cardiologist or radiologist will view the images, make a diagnosis, and prepare a diagnostic report. At times the images may be stored on a PACS archive server from which a physician can access the images for diagnosis. The workstation or terminal where the images are read may be equipped with special diagnostic software such as the QLAB diagnostic ultrasound analysis software package available from Philips Healthcare in Andover, Mass., USA, which facilitates the diagnosis of ultrasound images and the reporting of a diagnosis. When images are viewed on a new terminal or display screen, they are often not viewed under the same conditions as they were on the ultrasound system which acquired the images, causing subtle anatomic differences to appear differently. The review workstation or terminal may be in a more dimly or brightly lighted room, for instance, which will affect the appearance of the images in other environments. Different display screens will cause subtle image differences, as will the image file size and image compression which may be used to archive images. The physician could go through an adjustment procedure to optimize the images on the review terminal (e.g., GSDF) but this is usually not done due to its complexity and the time involved in evaluating different display options. Many doctors simply accept the factory default settings on their terminals and settle for sub-optimal images. Accordingly there is a need to simplify the optimization of a workstation, terminal or display screen for the optimal viewing of diagnostic ultrasound images which have been exported from the acquiring ultrasound system.

In accordance with the principles of the present invention, a diagnostic ultrasound system has a setup procedure that optimizes images for display on remote workstations, terminals, and display screens. The ultrasound system enables a user to select one ultrasound image acquired on the ultrasound system which is exported to a remote display terminal with a number of different display settings applied to the image. A user on the remote display terminal views a gallery of the same image with different display settings such as different display gamma correction, file sizes, brightness and/or contrast. The user then selects the image from the gallery with the best appearance on the remote terminal and the display parameters of the selected image are stored on the ultrasound system. Each time a new image or images are exported to the terminal, they are thereafter sent with the selected display settings, assuring that they will be remotely displayed as the remote user desires. Should the remote user have a change of mind or a new display with different characteristics be installed, the process can repeated to update the display parameters applied to images exported to the remote terminal.

Figure 1:
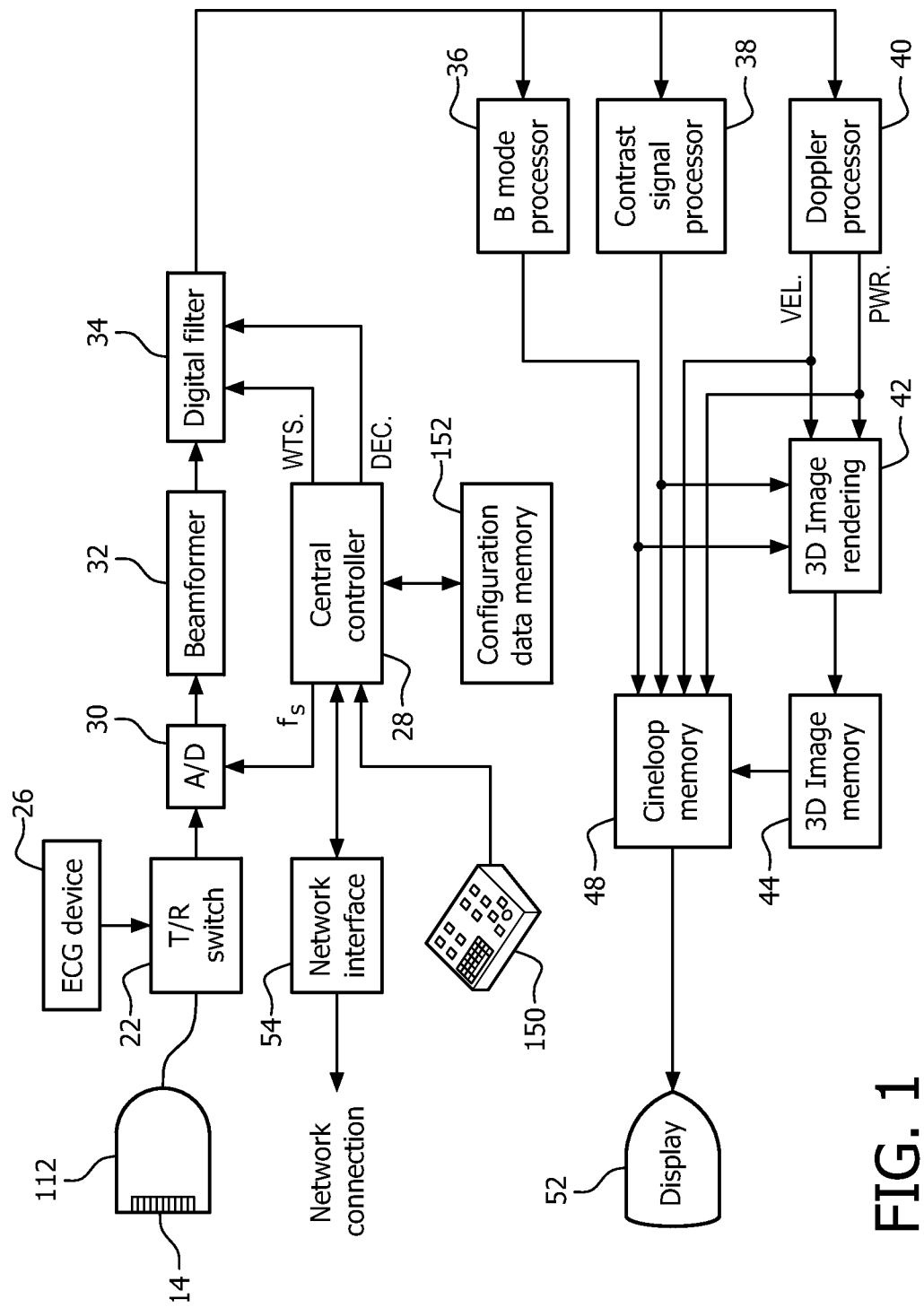
FIG. 1 illustrates in block diagram form an ultrasound system constructed in accordance with the principles of the present invention.

Referring first to FIG. 1 an ultrasonic diagnostic imaging system constructed in accordance with the principles of the present invention is shown in block diagram form. An ultrasound probe 112 includes an array 114 of ultrasonic transducers that transmit and receive ultrasound signals. The array may be a one dimensional linear or curved array for two dimensional imaging, or may be a two dimensional matrix of transducer elements for electronic beam steering in three dimensions. Three dimensional image data sets and images are preferably acquired using a two dimensional array transducer. Three dimensional images may also be acquired with a mechanically swept one dimensional array probe. The ultrasonic transducers in the array 114 transmit ultrasonic energy and receive echoes returned in response to this transmission. A transmit/receive ("T/R") switch 22 is coupled to the ultrasonic transducers in the array 114 and switches between the transmit and receive phases of pulse-echo imaging. The times at which the transducer array is activated to transmit signals may be synchronized to an internal system clock (not shown), or may be synchronized to a bodily function such as the heart cycle, for which a heart cycle waveform is provided by an ECG device 26. When the heartbeat is at the desired phase of its cycle as determined by the waveform provided by ECG device 26, the probe is commanded to acquire an ultrasonic image. The frequency and bandwidth of the ultrasonic energy transmitted by the transducer array is controlled by control signals generated by a central controller 28.

Echoes from the transmitted ultrasonic energy are received by the transducers of the array 114, which generate echo signals that are coupled through the T/R switch 22 and digitized by analog to digital ("A/D") converters 30 when the system uses a digital beamformer. Analog beamformers may also be used. The A/D converters 30 sample the received echo signals at a sampling frequency controlled by a signal $f_S$ generated by the central controller 28. The desired sampling rate dictated by sampling theory is at least twice the highest frequency of the received passband, and might be on the order of at least 30-40 MHz. Sampling rates higher than the minimum requirement are also desirable.

The echo signal samples from the individual transducers of the array 114 are delayed and summed by a beamformer 32 to form coherent echo signals. For 3D imaging with a two dimensional array, it is preferable to partition the beamformer between a microbeamformer located in the probe and the main beamformer in the system mainframe as described in U.S. Pat. No. 6,013,032 (Savord) and U.S. Pat. No. 6,375,617 (Fraser). The digital coherent echo signals are then filtered by a digital filter 34. In the illustrated system the transmit frequency and the receiver frequency are individually controlled so that the beamformer 32 is free to receive a band of frequencies which is different from that of the transmitted band such as a harmonic frequency band. The digital filter 34 bandpass filters the signals, and can also shift the frequency band to a lower or baseband frequency range. The digital filter could be a filter of the type disclosed in U.S. Pat. No. 5,833,613, for example. Filtered echo signals from tissue are coupled from the digital filter 34 to a B mode processor 36 for conventional B mode processing.

Filtered echo signals of a contrast agent, such as microbubbles, are coupled to a contrast signal processor 38. Contrast agents are often used to more clearly delineate the endocardial wall in relation to contrast agent in the blood pool of the heart chamber, or to perform perfusion studies of the microvasculature of the myocardium as described in U.S. Pat. No. 6,692,438 for example. The contrast signal processor 38 preferably separates echoes returned from harmonic contrast agents by the pulse inversion technique, in which echoes resulting from the transmission of multiple pulses to an image location are combined to cancel fundamental signal components and enhance harmonic components. A preferred pulse inversion technique is described in U.S. Pat. No. 6,186,950, for instance.

The filtered echo signals from the digital filter 34 are also coupled to a Doppler processor 40 for conventional Doppler processing to produce velocity and power Doppler signals. The output signals from these processors may be displayed as planar images, and are also coupled to a 3D image processor 42 for the rendering of three dimensional images, which are stored in a 3D image memory 44. Three dimensional rendering may be performed as described in U.S. Pat. No. 5,720,291, and in U.S. Pat. Nos. 5,474,073 and 5,485,842, all of which are incorporated herein by reference.

The signals from the contrast signal processor 38, the B mode processor 36 and the Doppler processor 40, and the three dimensional image signals from the 3D image memory 44 are coupled to a Cineloop® memory 48, which stores image data for each of a large number of ultrasonic images. The image data are preferably stored in the Cineloop memory 48 in sets, with each set of image data corresponding to an image obtained at a respective time. The image data in a data set can be used to display a parametric image showing tissue perfusion at a respective time during the heartbeat. The sets of image data stored in the Cineloop memory 48 may also be stored in a permanent memory device such as a disk drive or digital video recorder for later analysis. The images in the Cineloop memory are displayed on a display 52.

When a sonographer begins a particular ultrasound exam the sonographer will generally start by selecting the appropriate probe for the exam, such as a phased array probe for a cardiac exam or a curved linear array for an abdominal or OB exam. The sonographer may then set up and adjust all the imaging parameters for the exam by adjusting the switches and controls on the system control panel 150. Generally, however, the sonographer will configure the system by calling up the set of standard or previously customized parameters for the type of exam being commenced. These preset parameters are stored in a configuration data memory 152 and are applied to the central controller 28 when selected by the sonographer. The central controller then uses the imaging parameters, as adjusted by the sonographer, to set up and conduct the imaging procedure selected by the sonographer.

Figure 2:
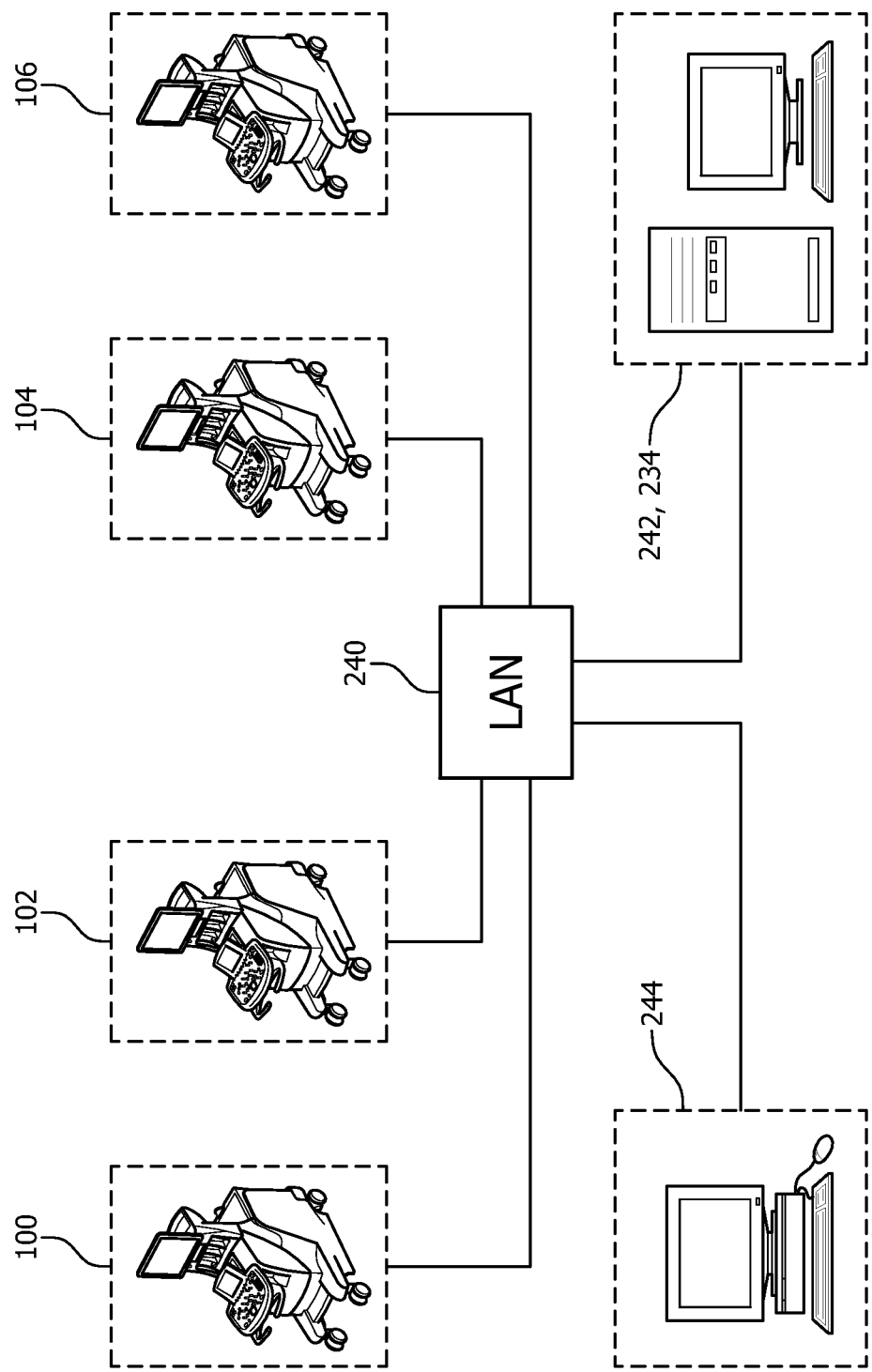
FIG. 2 illustrates an ultrasound system networked with a PACS system.

In larger hospitals and clinics the ultrasound system is generally connected to a network over which ultrasound images can be communicated. A network interface 54 enables the ultrasound system to communicate over the network and is coupled to a network connection in the hospital or clinic. A typical network with a PACS system is shown in FIG. 2. In FIG. 2, four ultrasound systems 102-106, a PACS image workstation 244, and a PACS network server 242 are connected in a local area network as indicated by LAN 240. The LAN 240 may be wired or wireless and may include both Ethernet hub systems and multi-switch, multi-layered networks. The network server 242 for a PACS system will have extended storage 234 for retention of a large volume of ultrasound images and reports produced by the network's ultrasound systems and image review stations. A user at the image workstation 244 can access the network server and individual active ultrasound systems of the network, or interact over the Internet with other externally accessible networks and devices.

In accordance with the principles of the present invention the ultrasound system of FIG. 1 is configured to export ultrasound images for viewing on a workstation or terminal on a network by use of an export configuration wizard illustrated in FIGS. 3a-3f. The starting screen of FIG. 3a informs the user that the wizard will guide them through the selection of various export configuration choices for an optimum configuration. The starting screen presents four topics for configuration. For an initial configuration all four topics are used. If the user wants to adjust a configuration that has been implemented previously, the user is given the choice of selecting only the topic(s) to be modified. The subsequent drawings illustrate an initial configuration setup.

Figure 3A:
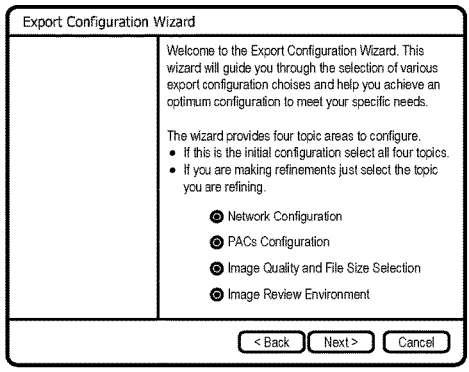
FIGS. 3a-3f illustrate display screens for setting up an ultrasound system on a network with user preferences for exported images.
Figure 3B:
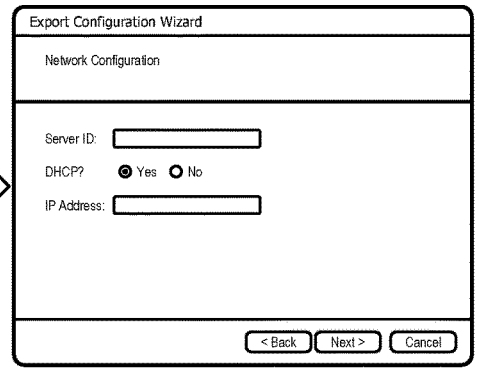

When the user clicks on the Next button of the starting screen the Network Configuration screen is presented as shown in FIG. 3*b*. On this screen the user can enter the identification of the network server. The next line on this screen allows the user to specify whether the DHCP (dynamic host configuration protocol) is being used, whether the ultrasound system will have a fixed IP address on the network or a variable (dynamic) IP address assigned by the host server. If the ultrasound system has a fixed IP address it is entered on the next line.

Figure 3C:
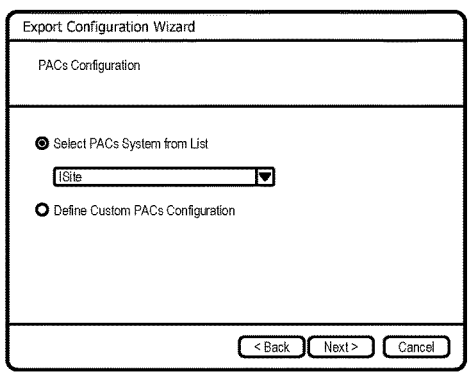

The user clicks the Next button and the PACs Configuration screen appears as shown in FIG. 3*c*. Here the user can select a PACS system from a pulldown list that is on the network and already identified by the wizard. Alternatively the user can click the Custom PACs Configuration radio button and is presented with a screen for entry of data that defines a custom PACS configuration. The user clicks the Next button and is presented with the FIG. 3*d* screen.

Figure 3D:
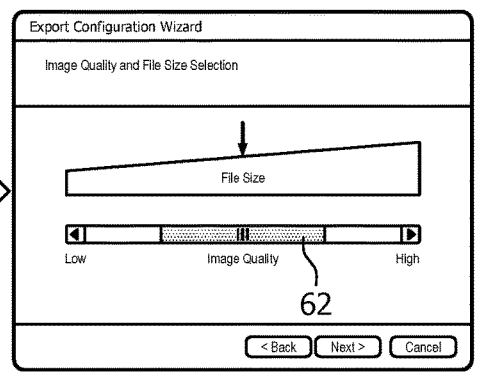
Figure 3E:
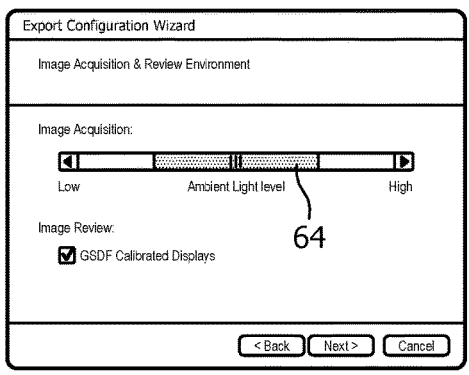

On the Image Quality and File Size Selection screen of FIG. 3*d* the user defines one of the parameters that affects how images exported from the ultrasound system appear on the screen of a workstation or terminal on the network. The PACS system or other storage device may store ultrasound images with a predetermined amount of compression or a file size limit. The size of the image file is directly related to the perceived image quality since finer detail can be shown in an image of a larger file size. In this example the user drags a slider 62 horizontally to set the desired image quality. An arrow above the File Size graphic moves correspondingly, showing the user the file size recommended for the desired image quality. The user will generally balance the desired image quality and file size to obtain the highest quality images within the bounds of the permitted size of images archived on the PACS system. The user clicks the Next button and is presented with the screen of FIG. 3*e*.

The Image Acquisition & Review Environment screen enables a user to set another parameter that affects how images acquired by the ultrasound system will appear on the remote terminal. The patient scanning room may be only dimly lighted and consequently the user may employ low brightness and contrast settings to view the ultrasound images as they are acquired. The physician reading the images may be viewing them in a brightly lighted room, which means that the view settings on the ultrasound system will not be suited to the ambient lighting conditions of the reading room. Or, the reverse may be true. With the screen of FIG. 3*e* the user can adjust slider 64 to indicate the ambient lighting conditions in the scanning room as low, high, or intermediate. The user can also check the GSDF (grayscale standard display function) box if the display at the remote terminal has this DICOM calibrated display function, in which case further display optimization is not necessary.

Figure 3F:
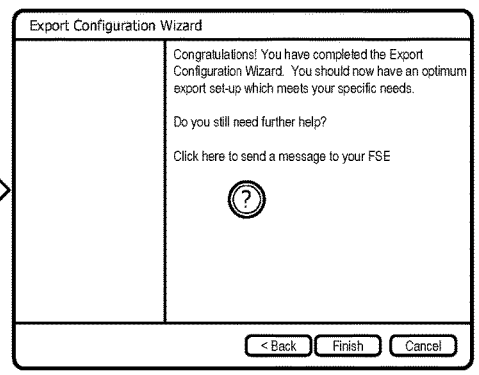

After the user has adjusted the last set of display parameters the user is presented with the closing screen of FIG. 3*f*. If the user has finished specifying the PACS and image export parameters the user can click on the Finish button to conclude the export configuration process. If the user has encountered a problem or has a question, the user can click on the question mark symbol to request technical assistance in completing the configuration process.

Figure 4:
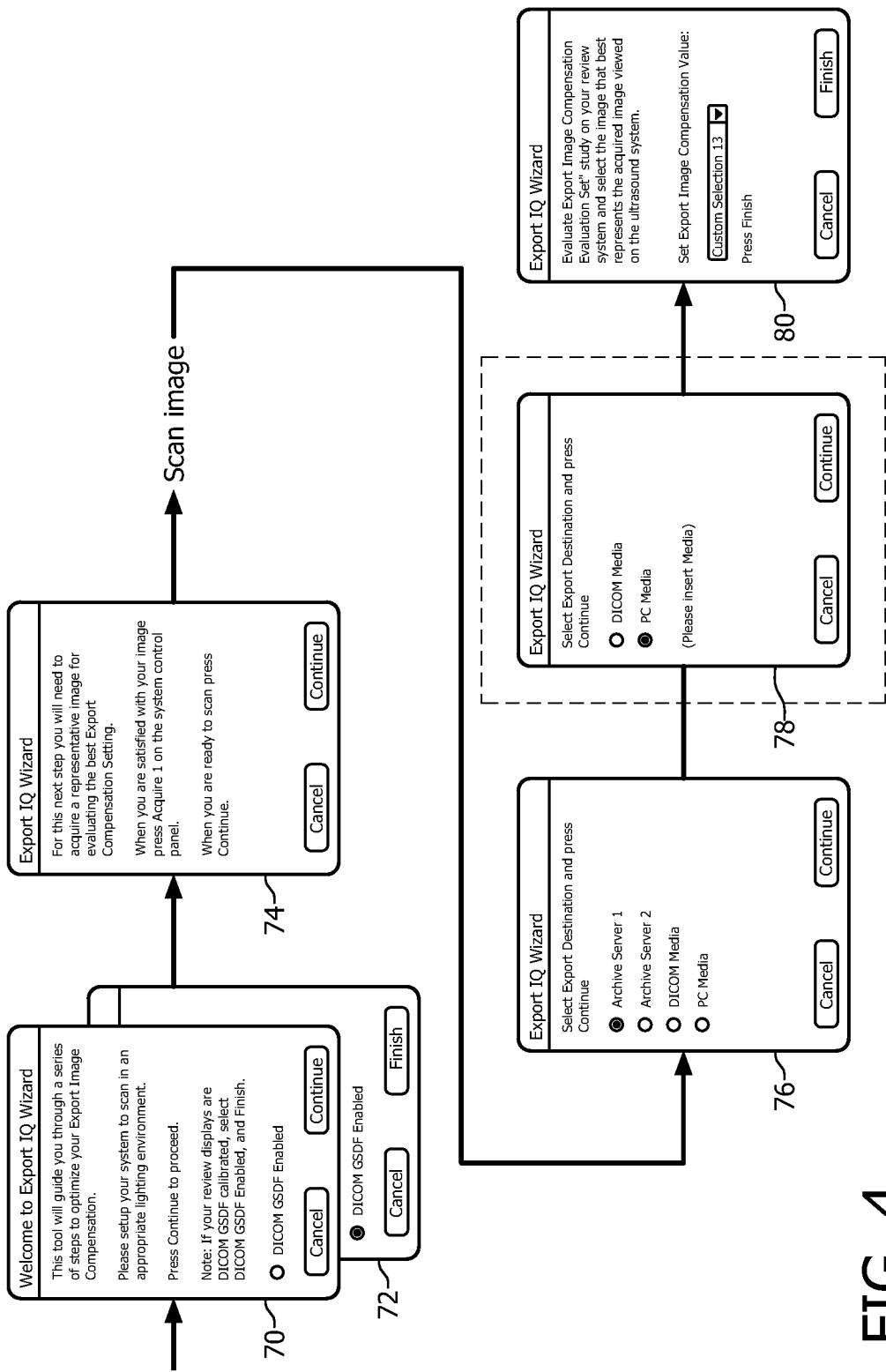
FIG. 4 illustrates a method for setting up and exporting a gallery of images with different display settings to a remote terminal.

With the export parameters and network protocols thus set, the user now prepares an export of images that will be displayed with different display parameters as exemplified by the export screens of FIG. 4. In this set of screens, identified as the Export IQ Wizard, the user is guided through the acquisition of an ultrasound image and its export with different processing for viewing and selection on a remote terminal. The first screen 70 instructs the user to prepare the ultrasound system to scan an image under the condition generally preferred by the user, such as in an appropriately lighted room. If the display at the remote terminal is DICOM GSDF calibrated, this compensation procedure is not needed, however. The user will then click the DICOM GSDF Enabled radio button and proceed to Finish this compensation procedure, as indicated by screen 72.

When the user clicks the Continue button on screen 70 to proceed with the compensation procedure, the user is shown screen 74. This screen instructs the user to acquire an ultrasound image with the ultrasound system. The user can do this by scanning a patient at this time, in which case the user will click the Continue button on screen 74 and will scan a subject. After the user has acquired a satisfactory image the user presses Acquire 1 on the ultrasound system control panel 150. Alternatively, the user can select a previously acquired satisfactory image from the image storage on the ultrasound system. Again, the user indicates that a satisfactory image has been obtained by pressing Acquire 1 on the ultrasound system control panel 150.

Figure 5:
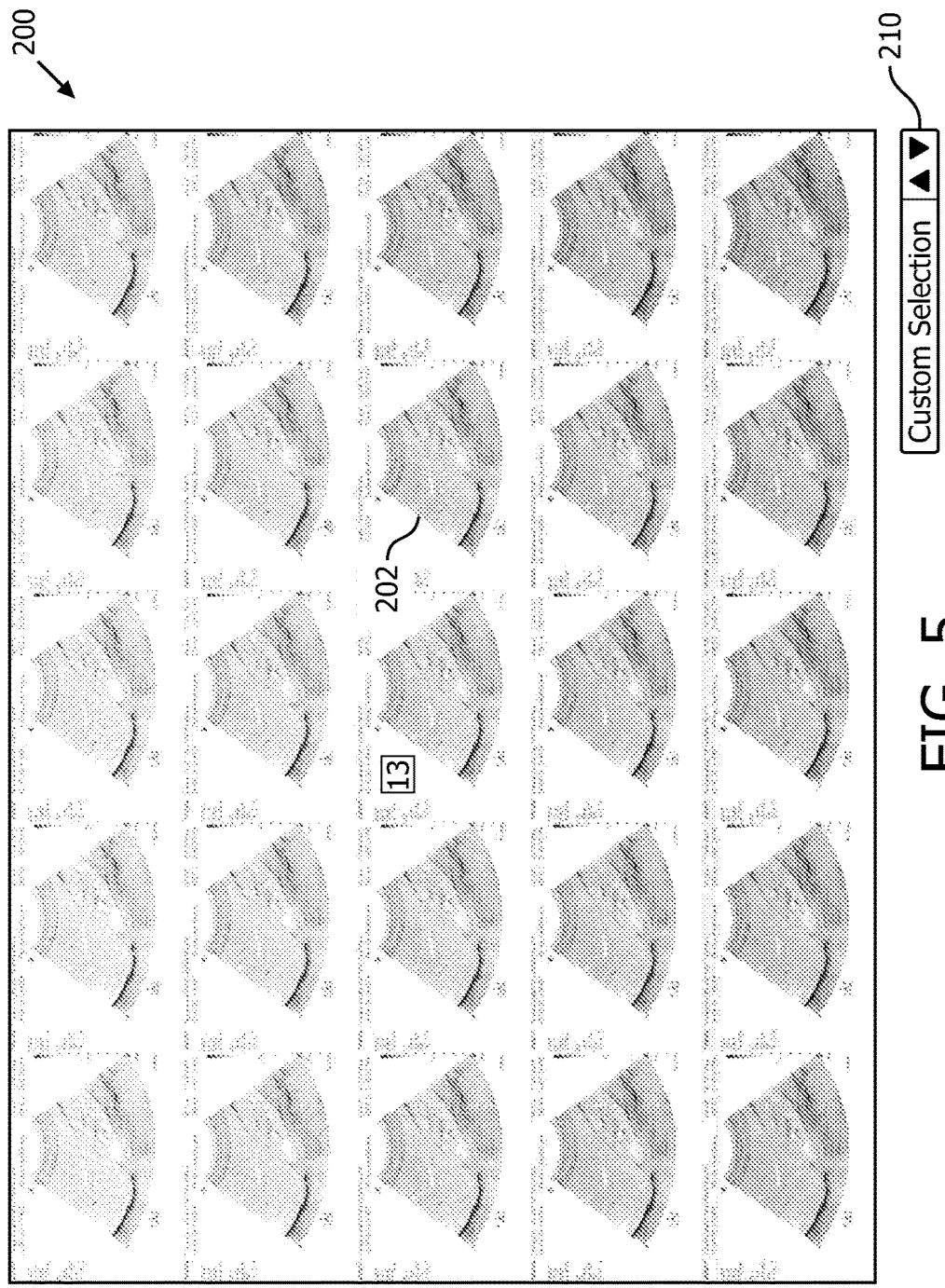
FIG. 5 illustrates a gallery of images with different display settings which are presented to a user for selection of the best image.

With the basic compensation image identified, the user selects a destination to which compensation selection images are to be exported using screen 76. In this example the user has selected Archive Server 1, a PACS image storage device on the network where the images are stored with the image processing employed by the PACS system. Screen 76 gives examples of different export destinations including one called PC Media for ultrasound systems not connected to a reading station by a network. If this radio button is selected the screen 78 appears to instruct the user to insert media into the ultrasound system such as a portable flash drive. The images are then transferred to the flash drive which can be carried to the reading workstation for the compensation setup. In this example the user has selected Archive Server 1 and a set of compensation images such as that of FIG. 5 is sent to the Archive Server 1 PACS system. Screen 80 is then displayed to the user, instructing the user to view the compensation images on the PACS system display terminal and select the image that best represents the basic image acquired by or selected on the ultrasound system.

FIG. 5 is an example of a set of compensation images 200 that are exported to the PACS system and viewed on a review station on the PACS system such as terminal 244 in FIG. 2. Each of the twenty-five compensation images has been processed by the controller 28 or contains slightly different display parameters that will affect its appearance on a display screen. For instance, each of the twenty-five images can be processed by a slightly different display device gamma correction characteristic. Or each image will have a slightly different brightness or contrast to compensate for different ambient lighting conditions. The user views all twenty-five images simultaneously on the remote terminal display screen and selects the one which appears the best on that display screen. The user can click on the up and down arrows in the selection box 210 at the bottom of the screen to select the number of the best image. In this example the user has selected image number 13. Alternatively the user can click on an image to select it, such as clicking on image 202 to select that image as the best compensated image.

When the user makes the selection the identity of the selection is sent back to the ultrasound system where the display parameters of the selected image are stored in a lookup table in the configuration data memory 152 of the system in association with the export destination device, Archive Server 1 in this example. Thereafter, whenever images are exported from the ultrasound system to Archive Server 1, the display parameters stored in the lookup table in memory for that PACS system are applied to the images prior to export so that they are properly compensated to appear on the PACS terminal just as they appeared on the ultrasound system. A reviewer on the PACS workstation will then be viewing an exported image with the same image quality and characteristics as seen by the sonographer who acquired the image.

Screen 80 of FIG. 4 also gives the user the ability to select the desired image from the screen on the ultrasound system. The user can make the selection on screen 80, then click the Finish button to conclude the image export compensation process.

A PACS system may have multiple review stations or terminals on the system and each may have a different display characteristic. In that event, the foregoing compensation process may be performed for each display device of each station or terminal. The ultrasound system will then use the correspondingly identified display station when exporting images for display on one of the terminals.

A review station or terminal can also be replaced or modified with a different display screen or used by a clinician with different viewing preferences, requiring that the compensation be performed again for the new or different display device or reviewer. In that event, the Export IQ Wizard of FIG. 4 can be called up on the ultrasound system to send a new set of compensation screens to the terminal and the compensation selection process performed again and new display parameters for the terminal stored in the configuration data memory 152. Alternatively, the clinician at the review station can send a query to the ultrasound system, requesting transmission of another set of compensation images. The user of the remote terminal can thereby adjust or update the display parameters of images exported from the ultrasound system without interrupting the workflow of the sonographer who is using the ultrasound system.

The present invention has applicability in other medical imaging modalities, particularly in the use of "secondary captures," image information which is derived from a primary diagnostic image. For example, an MRI image of the body may show an invasive instrument such as a biopsy needle which a clinician wants to view in well defined resolution. The optimization technique of the present invention can be used to optimize the displayed images for optimal viewing of this secondary capture, the needle in the MRI image.

What is claimed is:

1. A diagnostic ultrasound system which compensates images exported to a remote display terminal comprising:
    a display configured to effectuate presentation of one or more views of a graphical user interface, the one or more views comprising one or more fields configured to facilitate entry and/or selection, by a user, of information related to one or more of a network configuration, a PACs configuration, an image quality selection, an image file size selection, or an ambient light level;
    an ultrasound image storage device which stores an image of a single ultrasound image plane acquired by the ultrasound system;
    an image processor which produces a plurality of versions of the image of the single ultrasound image plane for export, each version having a different display appearance when the plurality of versions of the image of the single ultrasound image plane are viewed simultaneously;
    a remote terminal having a display screen on which the plurality of versions of the image of the single ultrasound image plane are displayed simultaneously;
    a selector, upon additional user input selects one of the versions of the image of the single ultrasound image plane;
    a data storage device which stores a parameter for the version of the selected image in association with an identifier of the remote terminal; and
    an export processor which processes images for export to the remote terminal with the parameter of the selected image.

2. The diagnostic ultrasound system of claim 1, wherein the parameter is one of display device gamma characteristic, image brightness or image contrast.

3. The diagnostic ultrasound system of claim 1, wherein the remote terminal further comprises a PACS system.

4. The diagnostic ultrasound system of claim 3, wherein the remote terminal further comprises a PACS system image archive.

5. The diagnostic ultrasound system of claim 3, wherein the remote terminal further comprises one of a plurality of workstations of a PACS system.

6. The diagnostic ultrasound system of claim 1, further comprising a network which connects the ultrasound system and the remote terminal.

7. The diagnostic ultrasound system of claim 1, wherein the remote terminal and the ultrasound system are not on a common network,
    wherein the plurality of versions of the image are exported to the remote terminal on portable media.

8. The diagnostic ultrasound system of claim 1, further comprising an input device by which ambient light condition data is input into the ultrasound system,
    wherein the image processor produces the plurality of versions of the image for export in consideration of the ambient light condition data.

9. The diagnostic ultrasound system of claim 1, further comprising an input device by which image file size data is input into the ultrasound system,
    wherein the image processor produces the plurality of versions of the image for export in consideration of the image file size data.

10. The diagnostic ultrasound system of claim 9, wherein the image file size further comprises the file size of images stored on a network image archive.

11. The diagnostic ultrasound system of claim 1, further comprising an input device by which image quality data is input into the ultrasound system,
    wherein the image processor produces the plurality of versions of the image for export in consideration of the image quality data.

12. The diagnostic ultrasound system of claim 1, wherein the data storage device stores the parameter for the version of the selected image in lookup table form.

13. The diagnostic ultrasound system of claim 1, wherein the production of a plurality of versions of the image for export is initiated from the ultrasound system.

14. The diagnostic ultrasound system of claim 1, wherein the production of a plurality of versions of the image for export is initiated from the remote terminal.

15. The diagnostic ultrasound system of claim 1, wherein the data storage device stores a plurality of parameters, each in association with an identifier of a different remote terminal;

wherein the export processor processes images for export in consideration of the identifier of one of the different remote terminals which is the destination of exported images.

\* \* \* \* \*